United States Patent
Stinson

(10) Patent No.: US 7,572,287 B2
(45) Date of Patent: Aug. 11, 2009

(54) BALLOON EXPANDABLE POLYMER STENT WITH REDUCED ELASTIC RECOIL

(75) Inventor: Jonathan S. Stinson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1718 days.

(21) Appl. No.: 10/037,036

(22) Filed: Oct. 25, 2001

(65) Prior Publication Data

US 2003/0083732 A1    May 1, 2003

(51) Int. Cl.
   *A61F 2/06*    (2006.01)
(52) U.S. Cl. ..................... 623/1.15; 264/235
(58) Field of Classification Search ....... 613/1.15–1.22, 613/1.11, 901; 606/108, 198, 154, 155; 264/567, 264/235, 235.6
   See application file for complete search history.

(56) References Cited

U.S. PATENT DOCUMENTS

| | | | |
|---|---|---|---|
| 4,655,771 A | 4/1987 | Wallsten | 623/1 |
| 4,816,029 A * | 3/1989 | Penny et al. | 623/2.19 |
| 4,911,165 A * | 3/1990 | Lennard et al. | 606/231 |
| 4,950,258 A | 8/1990 | Kawai et al. | 604/281 |
| 5,032,679 A | 7/1991 | Brandley et al. | 536/21 |
| 5,061,275 A | 10/1991 | Wallsten et al. | 623/1 |
| 5,061,281 A | 10/1991 | Mares et al. | 623/11 |
| 5,348,538 A | 9/1994 | Wang et al. | 604/96 |
| 5,484,444 A * | 1/1996 | Braunschweiler et al. | 623/1.11 |
| 5,500,013 A | 3/1996 | Buscemi et al. | 623/1 |
| 5,527,337 A * | 6/1996 | Stack et al. | 606/198 |
| 5,591,222 A | 1/1997 | Susawa et al. | 623/1 |
| 5,591,224 A | 1/1997 | Schwartz et al. | 623/1 |
| 5,645,559 A | 7/1997 | Hachtman et al. | 606/198 |
| 5,670,161 A * | 9/1997 | Healy et al. | 623/1.42 |
| 5,674,277 A * | 10/1997 | Freitag | 623/1.13 |
| 5,868,783 A * | 2/1999 | Tower | 606/198 |
| 5,968,092 A | 10/1999 | Buscemi et al. | 623/1 |
| 5,980,564 A * | 11/1999 | Stinson | 623/23.7 |
| 6,149,680 A * | 11/2000 | Shelso et al. | 623/1.11 |
| 6,156,254 A * | 12/2000 | Andrews et al. | 264/231 |
| 6,159,237 A | 12/2000 | Alt et al. | 623/1.11 |
| 6,174,330 B1 * | 1/2001 | Stinson | 623/1.34 |
| 6,245,103 B1 * | 6/2001 | Stinson | 623/1.22 |
| 6,368,346 B1 | 4/2002 | Jadhav | 623/1.22 |
| 6,626,939 B1 * | 9/2003 | Burnside et al. | 623/1.38 |
| 2001/0021871 A1 | 9/2001 | Stinson | |
| 2001/0029398 A1 | 10/2001 | Jadhav | |

FOREIGN PATENT DOCUMENTS

| | | |
|---|---|---|
| CA | 2025626 | 3/1991 |
| EP | 0256748 | 4/1987 |
| EP | 0 540 858 A1 | 5/1993 |
| EP | 0894505 | 8/1998 |
| WO | 98/03218 | 1/1998 |

* cited by examiner

*Primary Examiner*—Kevin T Truong
*Assistant Examiner*—Victor X Nguyen
(74) *Attorney, Agent, or Firm*—Vidas, Arrett & Steinkraus

(57) ABSTRACT

A process for forming a stent of a polymer material which includes the steps of:
   a) forming a generally tubular stent;
   b) radially expanding the stent to produce an expanded diameter stent; and then,
   c) annealing the expanded diameter stent to shrink its diameter to a reduced diameter.

28 Claims, 2 Drawing Sheets

BALLOON EXPANDABLE POLYMER STENT WITH REDUCED ELASTIC RECOIL

BACKGROUND OF THE INVENTION

The present invention relates generally to implantable, radially expandable medical prostheses which are frequently referred to as stents.

Stents are well known and commercially available. They are, for example, disclosed generally in U.S. Pat No. 4,655,771, Wallsten; U.S. Pat. No. 5,061,275, Wallsten et al., and U.S. Pat. No. 5,645,559, Hachtmann et al. Stent devices are used within body vessels of humans for a variety of medical applications. Examples include intravascular stents for treating stenoses, stents for maintaining openings in the urinary, biliary, tracheobronchial, esophageal, and renal tracts, and vena cava filters.

A delivery device is used to deliver the stent in a compressed state to a treatment site through vessels in the body. The flexible nature and reduced radius of the compressed stent enables it to be delivered through relatively small and curved vessels. In percutaneous transluminal angioplasty, an implantable endoprosthesis is introduced through a small percutaneous puncture site, airway, or port and is passed through various body vessels to the treatment site. After the stent is positioned at the treatment site, it is deployed by expansion to contact the vessel wall and the delivery device is removed. The stent remains in the vessel at the treatment site as an implant.

Stents must exhibit a relatively high degree of biocompatibility since they are implanted in the body.

Stents are typically made of metal, but have also been made using polymer materials of varied composition and in varied conformations obtained by a variety of processing techniques.

U.S. Pat. No. 5,500,013, Buscemi, et al., describes a biodegradable drug delivery vascular stent.

U.S. Pat. No. 5,527,337, Stack, et al., describes a bioabsorbable stent and method of making the same.

U.S. Pat. No. 5,591,222, Susawa, et al., describes a device for dilating ducts in vivo, comprising a balloon-tipped catheter to which a cylindrical stent prepared by knitting or braiding or weaving biodegradable fibers to easily reduce diameter of the cylinder to a predetermined value is attached in a compressed condition, a method for preparing the device and a stent.

U.S. Pat. No. 5,591,224, Schwartz, et al., describes a bioelastomeric intraluminal stent comprising fibrin and elastin capable of providing a treatment of restenosis.

U.S. Pat. No. 6,245,103, Stinson, describes a bioabsorbable self-expanding stent formed from helically wound and braided filaments of bioabsorbable polymers such as PLA, PLLA, PDLA, and PGA.

CA 2025626, describes a biodegradable infusion stent used to treat ureteral obstructions. The application describes an extruded material construction made of epsilon-caprolactone; glycoside and L(−) lactide. The document describes a method for incorporating radiopaque materials such as barium sulfate into the polymer.

U.S. Pat. No. 4,950,258, Kawai et al., describes a biodegradable molded product having a first shape. The molded product is deformed at an elevated deforming temperature to form a second shape. The product is then cooled. When the product is reheated to a prescribed temperature, the product recovers the first shape.

U.S. Pat. No. 5,032,679, Brandley et al., describes a glycosaminoglycoside (GAG) composition made of tetrasaccharide units derived from heparin/heparin sulfate. The composition has use in preventing proliferation of smooth muscle cells.

U.S. Pat. No. 5,061,281, Mares et al., describes a medical device made from a resorbable homopolymer derived from the polymerization of an α-hydroxy carboxylic acid. The resorbable homopolymer has an average molecular weight of from 234,000 to 320,000 as measured by gel permeation chromatography.

Balloon expandable polymer stents typically have high radial elastic recoil when the balloon pressure is released, which can cause the stent to retract away from the vessel wall and migrate. This is particularly a problem with biodegradeable polymer stents. One design approach for compensating for low material properties is to increase the thickness of the structural element. The drawback of this approach is that it conflicts with another common design goal of angioplasty devices which is to minimize profile so as to make as small a puncture for the introduction site in the patient as possible.

Therefore there is a need for a method of minimizing elastic recoil in expanded polymer stents, especially with biodegradeable polymer stents.

SUMMARY OF THE INVENTION

The invention is a novel method of manufacturing polymer stents with reduced elastic recoil. It may be used to provide an easily and accurately positionable bioabsorbable expandable stent with high polymer strength and stiffness to minimize radial elastic recoil.

The novel method of manufacturing the expandable stent is to pre-stretch and anneal the stent prior to expansion during implantation. Specifically, the stent is formed at an initial diameter. The formed stent is then radially expanded to a diameter that is larger than the original diameter so as to cause permanent elongation of the stent wall in the radial direction. This expansion is generally done at room or lower temperature. The enlarged stent is then annealed, typically while mounted on a tubular mandrel that is of the size of the desired finished manufactured design dimensions, to shrink the enlarged stent to the desired finished manufactured design dimensions. The enlarging and annealing/shrinking operation may be performed more than one time to increase the working and preferred molecular orientation of the material. When the finished stent is balloon dilated as in a stent angioplasty procedure, the stent of this invention will have less radial elastic recoil and higher resistance to radial compression (crush resistance) due to the increased preferred orientation of the molecular structure stent in the expanded state.

DESCRIPTION OF THE DRAWINGS

FIG. 1 shows a stent formed to diameter A

FIG. 2 shows the stent of FIG. 1, pre-expanded to a diameter B.

FIG. 3 shows the stent annealed to shrink to diameter C.

FIG. 4 shows the stent is implanted and expanded to diameter D.

FIG. 5 shows the stent recoil to a diameter E after release of balloon pressure.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

Self-expanding stents are desirable primarily because of small radial elastic recoil and dynamic radial force over the range of stent diameter from when it is constrained on the delivery system to expanded within the vessel. Unfortunately, some self expanding designs have rather long stent lengths when constrained on the delivery system and significant axial shortening during deployment and expansion. Balloon predilation and/or post-dilation is often necessary to assist the self-expansion of these stents. Balloon expandable stents are desirable primarily because with some designs there is little or no axial shortening during expansion and it is unnecessary to use a separate balloon catheter before and after stent deployment. Unfortunately, as already noted, balloon expandable polymer stents typically have high radial elastic recoil when the balloon pressure is released, which can cause the stent to retract away from the vessel wall and migrate.

The invention overcomes some of the disadvantages of balloon-expandable bioabsorbable stent designs, avoiding high radial elastic recoil by improving the radial strength and stiffness of the stent material beyond that of the current technology. The inventive stents will not necessarily require pre- and post-dilation with another balloon catheter, as is common with current self-expanding polymer stents; can be more accurately placed within strictures than current self-expanding polymer stents; will have better apposition of the stent to the vessel wall and be less prone to migration than current polymer balloon expandable stents; and will have higher radial strength and stiffness than current polymer balloon expandable stents. The stent implant of this invention will be easier to implant and will provide a stronger scaffold to hold open the obstruction. Therefore the inventive stents may provide improved clinical performance over the current bioabsorbable polymer stents.

The invention enhances the radial strength properties of balloon-expandable polymer stents by pre-stretching and annealing the stent to tailor the polymer material properties for the intended use, i.e., to provide a radially supportive structural tubular scaffold to brace open an occluded body vessel.

Referring to FIGS. 1-5, there is shown schematically a series of steps in the inventive method of optimizing the material properties in the radial orientation of the stent.

Figure 1:
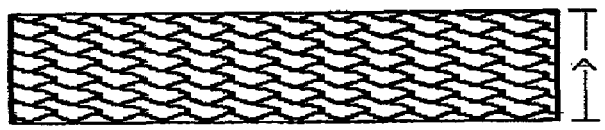
FIGS. 1-5 are schematic depictions of a polymer stent at various states of expansion in the course of processing and use.

In FIG. 1, the stent is formed to an initial diameter, A. Generally the stent will be formed by molding, but other techniques such as rolling and welding a pattern cut sheet or cutting a pattern in a cylindrical tube, may also be used.

Figure 2:
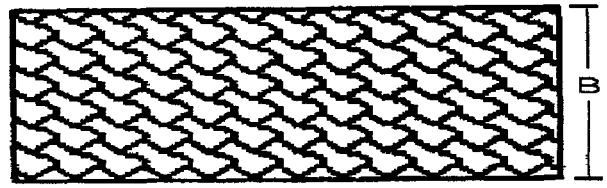
Figure 3:

The stent of diameter A is then mechanically radially expanded to a diameter that is larger than the original diameter A so as to cause permanent elongation of the stent wall in the radial direction to a new diameter, B, as shown in FIG. 2. This expansion step is suitably performed at a temperature below glass transition of the polymer material, typically about room temperature or even lower. The expansion may be accomplished on an expandable mandrel, such as an expandable collet, which is gradually enlarged until the desired diameter B had been reached. Alternatively a tapered mandrel which gradually increases in diameter to the new diameter B may be employed, sliding the stent up the taper until it reaches the expanded diameter. Another alternative expansion technique would be to use a balloon to expand the stent, suitably within a tube form to control the expansion profile.

The enlarged stent of diameter B is then slid onto a tubular mandrel that is of the size of the desired finished-manufactured design dimensions (diameter C, FIG. 3) and annealed at a temperature higher than that employed in the expansion step so that the material shrinks down onto the surface of the mandrel. Suitably the annealing temperature is near or above the glass transition temperature of the balloon material. The enlarging and annealing/shrinking operations of FIGS. 2 and 3 may be performed more than once to increase the working and preferred molecular orientation of the material.

Figure 4:
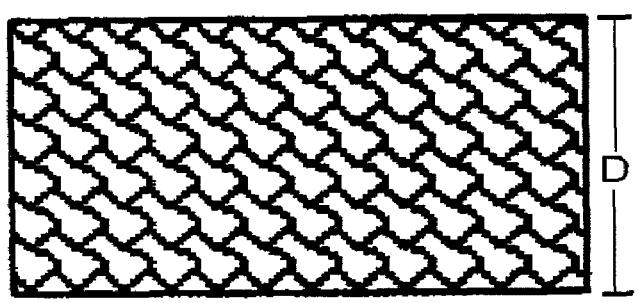
Figure 5:
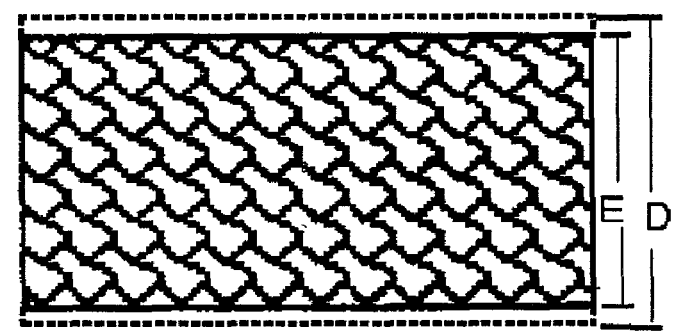

When the finished stent is balloon dilated, as in a stent angioplasty procedure, it expands from diameter C to the implant diameter D, FIG. 4. Upon removal of the balloon pressure, however, the stent will recoil to a reduced diameter E, shown in FIG. 5. The stents of the present invention have a reduced radial elastic recoil (typically expressed as a percentage, ie. $(D-E/D) \times 100$) and higher resistance to radial compression (crush resistance) due to the highly oriented molecular structure.

While the stents of the invention may be made from any implantable polymer material, suitably thermoplastic or only lightly crosslinked, preferred embodiments are made from bioabsorbable polymer, or substantially entirely bioabsorbable polymer. Suitable bioabsorbable polymers include poly (alpha-hydroxy acid) such as polylactide (PLA), poly-L-lactide (PLLA), poly-D-lactide (PDLA), polyglycolide (PGA), polydioxanone, polycaprolactone, poly(hydroxybutyrate), and polygluconate; polylactic acid-polyethylene oxide copolymers; modified cellulose; collagen or other connective proteins; adhesive proteins; hyaluronic acid; polyanhydrides; polyphosphoesters; poly(amino acids); copolymers thereof; and mixtures of any of the foregoing materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

Preferably the polymer materials used in the inventive stents are materials have been approved by the U.S. Food and Drug Administration for implantation within the body. Suitable bioabsorbable resins such as PLA, PLLA, PDLA, PGA and other bioabsorbable polymers are commercially available from several sources including PURAC America, Inc. of Lincolnshire, Ill.

Typically bioabsorbable PLLA and PGA material are degraded in vivo through hydrolytic chain scission to lactic acid and glycolic acid, respectively, which in turn is converted to $CO_2$ and then eliminated from the body by respiration. Heterogeneous degradation of semicrystalline polymers occurs due to the fact that such materials have amorphous and crystalline regions. Degradation occurs more rapidly at amorphous regions than at crystalline regions. This results in the product decreasing in strength faster than it decreases in mass. Totally amorphous, cross-linked polyesters show a more linear decrease in strength with mass over time as compared to a material with crystalline and amorphous regions. Degradation time may be affected by variations in chemical composition and polymer chain structures, and material processing. The inventive process, by increasing the overall crystallinity of the stent material, may increase degradation time within the body and/or prolong the period of time during which the implant will effectively stent a treatment site within the body.

Mechanical properties of polymers, including biodegradable polymers, generally increase with increasing molecular weight. For instance, the strength and modulus of PLA generally increases with increasing molecular weight. Degradation time generally decreases with decreasing initial molecular weight (i.e., a stent made of a low molecular weight polymer would be bioabsorbed before a stent made of a high molecular weight polymer). Low molecular weight PLA is generally more susceptible to thermo-oxidative degradation than high molecular weight grades, so an optimum molecular weight range should be selected to balance properties, degradation time, and stability. The molecular weight and mechanical properties of the material generally decreases as degradation progresses. PLA generally has a degradation time greater than 1 year.

PLA, PLLA, PDLA and PGA polymers may have bulk tensile strengths of from about 40,000 psi to about 120,000 psi, with a tensile strength of 80,000 psi being typical. For the present invention a tensile strength of from about 60,000 psi to about 120,000 psi is preferred.

Polydioxanone, polycaprolactone, and polygluconate may have bulk tensile strengths of from about 15,000 psi to about 60,000 psi, with a tensile strength of 35,000 psi being typical. For the present invention tensile strengths of these polymers is preferably above about 25,000, for instance from about 45,000 psi to about 60,000 psi.

PLA, PLLA, PDLA and PGA include tensile modulus of from about 400,000 pounds per square inch (psi) to about 2,000,000 psi; a tensile modulus of 900,000 psi is typical; and a preferred tensile modulus of from about 700,000 psi to about 1,200,000 psi. Polydioxanone, polycaprolactone, and polygluconate include tensile modulus of from about 200,000 psi to about 700,000 psi; a tensile modulus of 450,000 psi is typical; and a preferred tensile modulus of from about 350,000 psi to about 550,000 psi.

PLA has a glass transition temperature of about 60° C., so care should be taken not to store the inventive stents in environments where high temperature exposure may result in dimensional distortion.

The polymer stent may be molded to shape using any conventional polymer molding practice and technology. Molding techniques that are appropriate would include injection molding, blow molding, tubing extrusion and drawing, and sheet or film forming, rolling, and adhesion or welding into the tubular shape. The stent may be molded as a whole in one piece or as components which are assembled by further molding, adhesion, or welding.

Alternatively the stent may be formed from a tubular preform by laser cutting, or by chemical or solvent etching, for instance using a masking technique to protect the desired stent form or a printing technique to apply a degrading or sensitizing agent to areas of the tube which are desired to be removed.

The formed stent will typically have a generally tubular configuration with a diameter A which may be smaller than, the same as, or larger than the finished-manufactured stent diameter C. For example, one design scenario for producing a 5.0 mm diameter stent implant would be to mold the stent to an A diameter of 2.5 mm, expand the stent to a B diameter of 4.0 mm, and then anneal the stent so that it shrinks down onto a 1.9 mm diameter mandrel (C diameter). Upon implantation, the 1.9 mm diameter stent is expanded with an angioplasty balloon to a D diameter of 5.0 mm in the vessel. Making molded stent diameter A smaller or larger than the finished-manufactured stent diameter C will affect the amount of conditioning that the material is subjected to for tailoring radial properties. If A is smaller than C, there will be less total conditioning. If A is larger than C, there will be more total conditioning.

The purpose of expanding the molded stent during manufacturing is to plastically stretch the material circumferentially by the application of radial expansion force so as to cause the molecular structure of the polymer to orient itself around the hoop. Stretching of polymer materials that are not significantly crosslinked causes the molecules to align in the direction of the elongation. This mechanical molecular orientation would add anisotropy to the material by creating more hoop orientation instead of axial or spiral orientations. The material will be stronger and stiffer when loaded in the direction of the oriented molecules. The expansion step should be performed at a temperature below the glass transition temperature of the material. Room temperature is usually suitable.

Figure 6:
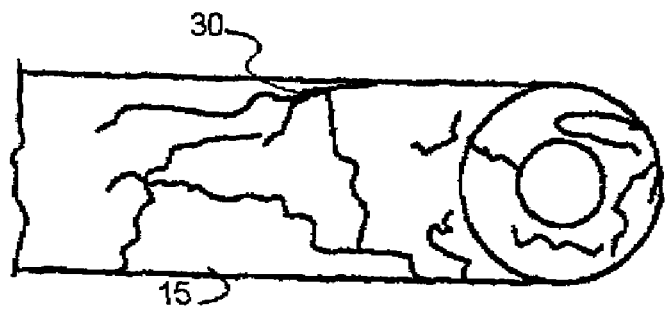
FIGS. 6 and 7, respectively, are schematic representations of molecular orientation in a formed polymer tube and in an expanded polymer tube.
Figure 7:
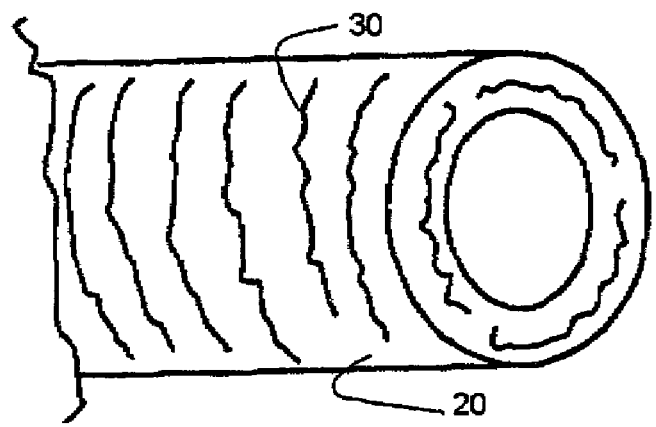

The orientation which is produced by the process of the invention is illustrated by FIGS. 6 and 7. FIG. 6 depicts a random molecular orientation in a molded polymer tube. A molded polymer stent will have a similar random molecular orientation. FIG. 7 shows that the polymer molecules become oriented in the hoop direction after radial expansion and circumferential stretching.

The stent will be stronger and stiffer under radial loading when in the condition shown in FIG. 7. Conversely, the stent will be less strong when loaded in an axial orientation, because the molecular rings can separate from each other. However, stent implant loading is primarily in the radial direction, and not significantly in the axial direction.

Annealing is performed at a temperature above the radial expansion step, typically above glass transition of the formed material, but below melt temperature. For purposes of the present invention glass transition temperature may be taken as determined by DSC. Suitably the temperature will be from about 5° C. to about 100° C. above glass transition. For example, a suitable annealing temperature for PLA, which has a $T_g$ of about 65° C., is in the range of 90-150° C. The purpose of the annealing operation is to reduce or eliminate residual elastic stresses present from the stretching operation and to allow the material to shrink fit onto a mandrel which has the size and shape of the finished manufactured stent. Some loss of molecular orientation will occur during annealing, but there will still be more orientation after stretching and annealing than before these operations were performed. Consequently, a higher degree of radial orientation is obtained when the stent is finally expanded within the body. Repeating the stretching and annealing operations one or more times at the same or different enlarged diameters B and shrunken diameters C will tend to further increase the final molecular orientation.

One example processing scenario for making a 5 mm diameter stent implant is to start with a molded poly-L-lactide tube with an A diameter of 1.5 mm, a first expanded diameter B of 3.0 mm, a first annealed diameter C of 1.9 mm, a second expanded diameter B of 3.2 mm, and a second annealed diameter C of 1.9 mm. Then during implantation the 1.9 mm stent would be expanded to 5 mm diameter D.

Another example of a process scenario for a 5 mm diameter stent implant to further increase molecular orientation, and tensile strength, and to minimize the elastic radial recoil from more stretching is to start with a molded poly-L-lactide tube with an A diameter of 1.5 mm, a first expanded diameter B of 4.5 mm, a first annealed diameter C of 1.7 mm, a second expanded diameter B of 5.0 mm, and a second annealed diameter C of 1.9 mm. Then during implantation the 1.9 mm stent is expanded to 5 mm diameter D.

Annealing temperatures appropriate for stretched poly-1-lactide material may range from 90° C. to 150° C. An example of a suitable annealing process is to heat the molded and stretched poly-1-lactide tube to 120° C. for 15 minutes on a mandrel of desired dimension, as described above.

Excessive heating during the annealing step(s) should be avoided to minimize reduction in the polymer's average molecular weight with consequent reduction in strength and other physical and chemical properties. For a given stent polymer and configuration, the optimum annealing temperature and time can be determined by subjecting the stretched tubes to various temperatures and times in order to find the set of process parameters that produces the desired shrinkage of the material onto the tubular mandrel and the least amount of reduction in molecular weight of the material.

The finished stent diameter, C, is chosen to be compatible with the desired delivery system profile and balloon size. The invention is advantageous in this regard, since by optimizing stent material properties the wall thickness can be kept low.

After the final annealing/shrinkage step, the stent may be modified if desired, e.g. by coating some or a portion thereof with a lubricious coating, or by impregnating or coating with a suitable drug. Preferably such modifications do not materially alter the physical properties of the stent. The stent, alone or mounted on a delivery catheter, is also sterilized before implantation. Ethylene oxide sterilization process (EtO) is a preferred method of sterilization for stents of the invention.

While the physician may load the stent onto a balloon catheter of preference, if desired, the invention also allows the stent to be loaded onto the delivery system by the manufacturer instead of by the physician such as is done with self-expanding stents. This makes it easier for the physician to use since he or she will not have to be bothered with a tedious preparation of the device for use.

To mount the stent on a catheter, either before sterilization or at the time of implantation, the stent is slid onto the balloon delivery catheter and held in place by mechanical crimping thereof onto the balloon or with a temporary adhesive or mechanical retaining mechanism such as a full length or partial length sheath or end sleeves.

To implant the stent, the balloon catheter with the inventive stent mounted thereon is passed through body vessels to the implant site just as is done with current angioplasty stents. Once positioned within the obstruction, the balloon is inflated and the stent is expanded. When the stent is opened to the desired size, the balloon pressure is released and the catheter is withdrawn leaving the stent in place as an implant. In the case of a biodegradable polymer stent, over a period of time the stent material degrades and is either excreted or absorbed. Desirably the material is selected to have a useful lifetime within the body which is sufficient to allow the body to heal the treatment site, but not so long as to cause substantial negative side-effects. The bioabsorbable stent thereby acts as a self-removing temporary stent and once removed there is no longer any concern about potential harmful interaction between the stent and the host as may be a risk with permanent stent implants.

Bioabsorbable polymer stents are radiolucent and the mechanical properties of the polymers are generally lower than structural metal alloys. Bioabsorbable stents may require radiopaque markers and may have a larger profile on a delivery catheter and in a body lumen to compensate for the lower material properties. A bioabsorbable marker that may advantageously be used in conjunction with the present invention is disclosed in U.S. Pat. No. 6,174,330.

While the invention has been described herein in conjunction with stent preparation, it should also be recognized that polymeric tubular articles in general may benefit from processing in accordance with the present invention in order to obtain enhanced radial strength and crush resistance. Such benefits may be especially useful with tubular medical devices, particularly medical devices adapted for body lumen navigation and treatment, including various catheters and catheter balloons. Thus in a further aspect the invention is a process for forming a tubular article of a polymer material, the process comprising the steps of:

a) forming a generally tubular article of said polymeric material;

b) radially expanding the article to produce an expanded diameter article; and then, c) annealing the expanded diameter article to shrink its diameter to a reduced diameter.

and wherein at least one time steps b) and c) are repeated in sequence and/or the polymer material is a biodegradable polymer as previously described. Stents may also be formed from tubing processed at least in accordance with steps a), b) and c), optionally with one or more repeats of steps b) and c), by machining or etching the processed tubing to stent form after the tubing processing steps.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A process comprising the steps of:
    a) forming a generally tubular stent of polymer material;
    b) radially expanding the stent to produce an expanded diameter stent; and then,
    c) annealing the expanded diameter stent to shrink its diameter to a reduced diameter, wherein the steps a)-c) are all performed prior to deployment of the stent in a body.

2. A process as in claim 1 further comprising at least one time repeating steps b) and c) in sequence on said stent.

3. A process as in claim 1 wherein in step a) the stent is formed by molding the polymer material.

4. A process as in claim 3 wherein the polymer material is thermoplastic.

5. A process as in claim 4 wherein the polymer material is biodegradable.

6. A process as in claim 1 wherein the polymer material is selected from the group consisting of poly(alpha-hydroxy acid), polylactic acid-polyethylene oxide copolymers; modified cellulose; collagen or other connective proteins; adhesive proteins; hyaluronic acid; polyanhydrides; polyphosphoesters; poly(amino acids); copolymers thereof; and mixtures of any of said materials.

7. A process as in claim 6 wherein the polymer material is a poly(alpha-hydroxy acid) selected from the group consisting of homopolymers and copolymers of polylactide (PLA), poly-L-lactide (PLLA), poly-D-lactide (PDLA), polyglycolide (PGA), polydioxanone, polycaprolactone, poly(hydroxybutyrate), polygluconate, and mixtures thereof.

8. A process as in claim 1 wherein the step b) is performed at a temperature below the glass transition temperature of the polymer material.

9. A process as in claim 8 wherein the step b) is performed at room temperature.

10. A process as in claim 1 wherein the step c) is performed at a temperature above the glass transition temperature of the polymer material.

11. A process as in claim 10 wherein the step c) is performed at a temperature within the range of about 90° C. to about 150° C.

12. A process as in claim 1 wherein in step a) a pattern of perforations is provided in the tube wall.

13. A process comprising the steps of:
    a) forming a generally tubular article of polymeric material;
    b) radially expanding the article to produce an expanded diameter article; and then,
    c) annealing the expanded diameter article to shrink its diameter to a reduced diameter,
wherein the steps a)-c) are all performed prior to deployment of the tubular article in a body, and wherein at least one time steps b) and c) are repeated in sequence on said tubular article.

14. A medical device adapted for body lumen navigation and/or treatment produced by the process of claim 13.

15. A process comprising the steps of:
    a) forming a generally tubular article of polymeric material;
    b) radially expanding the article to produce an expanded diameter article; and then,
    c) annealing the expanded diameter article to shrink its diameter to a reduced diameter,
wherein the steps a)-c) are all performed prior to deployment of the tubular article in a body, and wherein the polymer material is a biodegradable polymer.

16. A process as in claim 15 wherein at least one time steps b) and c) are repeated in sequence on said tubular article.

17. A process as in claim 15 wherein the polymer material is selected from the group consisting of poly(alpha-hydroxy acid), polylactic acid-polyethylene oxide copolymers; modified cellulose; collagen or other connective proteins; adhesive proteins; hyaluronic acid; polyanhydrides; polyphosphoesters; poly(amino acids); copolymers thereof; and mixtures of any of said materials.

18. A medical device adapted for body lumen navigation and/or treatment produced by the process of claim 15.

19. A process comprising the steps of:
    a) forming a tube of polymeric material;
    b) radially expanding the tube to produce an expanded diameter tube;
    c) annealing the expanded diameter tube to shrink its diameter to a reduced diameter; and subsequently
    d) forming a stent from the annealed tube,
wherein the steps a)-d) are all performed prior to deployment of the stent in a body.

20. A process as in claim 19 wherein the steps b) and c) are repeated at least once on said tube before step d) is performed.

21. A process as in claim 19 wherein in step d) the stent is formed by machining or etching the reduced diameter tube obtained from step c).

22. A process comprising the steps of:
    a) forming a generally tubular article;
    b) radially expanding the tubular article to produce an expanded diameter tubular article; and
    c) annealing the expanded diameter tubular article to shrink its diameter to a reduced diameter,
the process further comprising
    d) forming the tubular article as a stent with a pattern of perforations therein.

23. A process as in claim 22 wherein the tubular article formed with said pattern of perforations before said radially expanding step b).

24. A process as in claim 22 wherein the tubular article formed with said pattern of perforations after said annealing step c).

25. A process as in claim 22 further comprising at least one time repeating steps b) and c) on said tubular article.

26. A process as in claim 22 wherein the tubular article is formed of thermoplastic polymer material.

27. A process as in claim 26 wherein the step b) is performed at a temperature below the glass transition temperature of the polymer material.

28. A process as in claim 22 wherein the tubular article is made of biodegradable polymer material.

* * * * *

UNITED STATES PATENT AND TRADEMARK OFFICE
CERTIFICATE OF CORRECTION

PATENT NO.       : 7,572,287 B2                                           Page 1 of 1
APPLICATION NO.  : 10/037036
DATED            : August 11, 2009
INVENTOR(S)      : Stinson It is certified that error appears in the above-identified patent and that said Letters Patent is hereby corrected as shown below:

On the cover page,

[*] Notice:    Subject to any disclaimer, the term of this patent is extended or adjusted under 35 USC 154(b) by 1718 days.

Delete the phrase "by 1718 days" and insert -- by 1632 days --

Signed and Sealed this

Tenth Day of August, 2010

David J. Kappos
*Director of the United States Patent and Trademark Office*